United States Patent
Boyer et al.

(10) Patent No.: US 10,047,108 B2
(45) Date of Patent: Aug. 14, 2018

(54) PLATINUM (II) DIENE COMPLEXES WITH CHELATING DIANIONIC LIGANDS AND THEIR USE IN HYDROSILYLATION REACTIONS

(71) Applicant: MOMENTIVE PERFORMANCE MATERIALS INC., Waterford, NY (US)

(72) Inventors: Julie L. Boyer, Watervliet, NY (US); Aroop K. Roy, Mechanicville, NY (US); David Jenkins, Cohoes, NY (US); Indraneel Kundu, Clifton Park, NY (US)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 14/969,500

(22) Filed: Dec. 15, 2015

(65) Prior Publication Data

US 2017/0057980 A1   Mar. 2, 2017

Related U.S. Application Data

(60) Provisional application No. 62/210,607, filed on Aug. 27, 2015.

(51) Int. Cl.
| | |
|---|---|
| *C07F 7/08* | (2006.01) |
| *C07F 7/18* | (2006.01) |
| *B01J 31/16* | (2006.01) |
| *C07F 15/00* | (2006.01) |

(52) U.S. Cl.
CPC ............. *C07F 7/0829* (2013.01); *B01J 31/16* (2013.01); *C07F 7/0852* (2013.01); *C07F 7/0879* (2013.01); *C07F 7/1836* (2013.01); *C07F 7/1876* (2013.01); *C07F 15/0086* (2013.01)

(58) Field of Classification Search
CPC ........ C07F 7/0829; C07F 7/1876; C07F 7/08; C07F 7/18; C07F 15/00; B01J 31/16
USPC .......................................... 549/215; 556/479
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,775,452 A | 11/1973 | Karstedt | |
| 6,605,734 B2 | 8/2003 | Roy et al. | |
| 2006/0135689 A1* | 6/2006 | Fehn | ....................... B01J 31/185 524/862 |
| 2016/0030932 A1* | 2/2016 | Choi | ...................... B01J 37/086 423/700 |

FOREIGN PATENT DOCUMENTS

| | | |
|---|---|---|
| EP | 1672031 A1 | 12/2004 |
| WO | 2014142252 A1 | 3/2013 |
| WO | 2016044732 A1 | 9/2014 |

OTHER PUBLICATIONS

Speier, et al., "The Addition of Silicon Hydrides to Olefinic Double Bonds. Part II. The Use of Group VIII Metal Catalysts," J. Am. Chem. Soc., vol. 79, pp. 974-979. (1957).
Roy and Taylor, "The First Alkene-Platinum-Silyl Complexes: Lifting the Hydrosilation Mechanism Shroud with Long-Lived Precatalytic Intermediates and True Pt Catalysts," J. Am Chem. Soc., vol. 124, No. 32, pp. 9510-9524. (2012).
Boyer et al., "Redox Activation of Alkene Ligands in Platinum Complexes with Non-innocent Ligands," Inorganic Chemistry, vol. 48, No. 2, pp. 638-645. (2009).
Lewis et al., "Platinum-Catalyzed Hydrosilylation of Alkynes," Organometallics, vol. 10, No. 10, pp. 3750-3759. (1991).
Caseri and Pregosin, "Hydrosilylation Chemistry and Catalysis with cis-PtCl2 (PhCH=CH2)2," Organometallics, vol. 7, No. 6, pp. 1373-1380. (1988).
Don et al., "Synthesis, redox properties, and X-ray diffraction structure of the plantinum catecholate complex Pt(1,5-COD)(1,2-O2C6H4)," Journal of Chemical Crystallography, vol. 26, No. 5, pp. 335-340. (1996).
Patent Cooperation Treaty (PCT), International Search Report and Written Opinion for Application PCT/US2016/048252 filed Aug. 24, 2016, dated Nov. 23, 2016, International Searching Authority, EP.

* cited by examiner

*Primary Examiner* — Taylor V Oh
(74) *Attorney, Agent, or Firm* — Joseph Waters; McDonald Hopkins LLC

(57) ABSTRACT

A process for the hydrosilylation of an unsaturated compound comprising reacting (a) a silyl hydride with (b) an unsaturated compound in the presence of (c) a platinum based hydrosilylation catalyst comprising a platinum-diene complex with chelating anions. The use of the present catalysts in the process provides silylated products in good yields and allows for using lower platinum loadings than conventional catalysts, reduced cycle times, and may reduce yellowing in the product.

23 Claims, No Drawings

PLATINUM (II) DIENE COMPLEXES WITH CHELATING DIANIONIC LIGANDS AND THEIR USE IN HYDROSILYLATION REACTIONS

CROSS-REFERENCE TO RELATED APPLICATIONS

The present application claims priority to and the benefit of U.S. Provisional Application No. 62/210,607, filed on Aug. 27, 2015, the disclosure of which is incorporated herein by reference in its entirety.

FIELD OF THE INVENTION

The present invention relates generally to the use of platinum (II) diene complexes with chelating anions to catalyze hydrosilylation reactions.

BACKGROUND

Hydrosilylation chemistry, involving the reaction between a silylhydride and an unsaturated organic group, is the basis for synthetic routes to produce commercial silicone products such as silicone surfactants, silicone fluids and silanes. Conventionally, hydrosilylation reactions have been catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal compounds and complexes are widely employed commercially as catalysts for hydrosilylation reactions, they have several distinct disadvantages. One disadvantage of the conventional catalyst systems is the undesired color imparted to the final product. This yellow coloration or Pt precipitation in crude products often necessitates additional and costly purification steps. Another distinct disadvantage of the conventional systems is the progressive deactivation of the platinum catalysts during the course of the reaction which necessitates higher loadings of this costly metal.

Due to the high price of precious metals, catalysts derived from these platinum metals can constitute a significant proportion of the cost of organosilane and silicone products. Over the last two decades, global demand for precious metals, including platinum, has sharply increased, driving prices several hundred folds higher, thereby precipitating the need for effective, yet lower catalyst loadings. There is a need in the silicone industry for platinum catalysts of improved stability. This improved stability would enable the lowering of Pt catalyst loadings and decreasing cycle time in reactors and improving yield for many hydrosilylations.

The use of pre-formed Pt-COD complexes (COD=1,5-cyclooctadiene) in hydrosilylation reactions has been previously reported, e.g., L. Lewis et al., Organometallics, 1991, 10, 3750-3759, and P. Pregosin et al., Organometallics, 1988, 7, 1373-1380. $PtCODCl_2$, $PtCODMe_2$, and $PtCODPh_2$ are commercially available and their use as catalysts for hydrosilylation has been known for many years. Roy et al. have reported the preparation of a series of $PtCOD(SiR_3)_2$ compounds from $PtCODCl_2$ (Roy, Aroop K.; Taylor, Richard B. J. Am Chem. Soc., 2012, 124, 9510-9524; and U.S. Pat. No. 6,605,734).

Pt-COD complexes with catecholate or amidophenolate ligands have been reported (Boyer et al. Inorg. Chem 2009, 48, 638-645.; Richmond et al, J. Chem. Crystallogr. 1996, 26, 335-340). These papers describe the redox reactivity of these Pt complexes with non-innocent ligands. The use of these platinum-diene complexes with chelating dianions in hydrosilylation reactions producing organofunctional silanes and fluids has not been reported.

There is a need in the silicone industry for platinum catalysts of improved stability as industry work-horse catalysts such as Speier's and Karstedt's are prone to partial deactivation via agglomeration, especially at elevated temperatures of use. Improved stability of the active catalyst would enable the lowering of Pt catalyst loadings. In addition to improved stability, catalysts that demonstrate rapid activation and high hydrosilylation activity at elevated temperature are especially sought. Lastly, platinum catalysts are needed that have improved solubility in industrially-preferred organic solvent or silicones. The present invention provides one solution to these needs.

SUMMARY

The present invention provides the use of platinum-diene complexes with chelating dianionic ligands in hydrosilylation reactions. It has been found that platinum-diene complexes with chelating dianionic ligands are suitable for use in hydrosilylation reactions and exhibit acceptable to very good activity at low platinum loadings. The stabilization can be observed, for example, by the ability to use lower platinum loadings in hydrosilylation reactions, improved color of the hydrosilylation products, reduce reaction time and/or reduction of side reactions occurring during the process.

In one aspect, the present technology provides a process for the hydrosilylation of an unsaturated compound comprising reacting (a) a silyl hydride with (b) an unsaturated compound in the presence of (c) a hydrosilylation catalyst, optionally in the presence of a solvent, in order to produce the hydrosilylated product, wherein the hydrosilylation catalyst is a complex of Formula (I):

(I)

where $R^1$—$X^2$—$R^2$ is a diene that is bonded to platinum in an $\eta^4$-mode and is chosen from a branched or unbranched chain, a cyclic structure, or a bicyclic system having 4 to 30 carbon atoms, whereby the diene comprises bonding olefin moieties that are terminal and/or internal, and $X^2$ represents one or more bridges between the olefinic groups;

$E^1$ and $E^2$ are independently chosen from a mono-anionic group of O, $NR^3$, carboxyl group (C(O)O), and S; $R^3$ is independently hydrogen, or a monovalent hydrocarbon radical having from 1 to 30 carbon atoms;

$X^1$ is a divalent hydrocarbyl or silicone group chosen from a substituted or unsubstituted alkylene, an arylene, or a siloxanylene group;

$X^2$ is a divalent hydrocarbyl group chosen from a substituted or unsubstituted alkylene, an arylene, or a cycloalkylene group; and n is 0, 1, 2, 3, or 4.

In one embodiment, $E^1$ and $E^2$ are O.

The process of any previous embodiment, wherein $R^1$—$X^2$—$R^2$ is 1,5-cyclooctadiene.

The process of any previous embodiment, wherein $E^1$-$X^1$-$E^2$ is chosen from an amidophenolate, a phenylenediamide, a benzenedithiolate, a mercaptophenolate, a mercaptoethanolate, a pinacolate, an ethylene diolate, a propandiolate, a catecholate, a substituted catecholate, a salicylate, an oxalate, or malonate.

The process of any previous embodiment, wherein $R^1$—$X^2$—$R^2$ is 1,5-cyclooctadiene.

The process of any previous embodiment, wherein $E^1$-$X^1$-$E^2$ is represented by the formula:

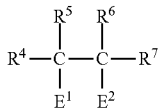

where $R^4$, $R^5$, $R^6$, and $R^7$ are independently chosen from hydrogen, a C1-C20 alkyl, and a C6-C10 aryl.

The process of any previous embodiment, wherein $E^1$-$X^1$-$E^2$ is represented by the formula:

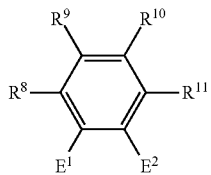

where $R^8$, $R^9$, $R^{10}$, and $R^{11}$ are independently chosen from hydrogen and a C1-C20 alkyl.

The process of any previous embodiment, wherein $R^8$, $R^9$, $R^{10}$, and $R^{11}$ are each hydrogen.

The process of any previous embodiment, wherein $R^8$ and $R^{10}$ are independently chosen from a C1-C20 alkyl, and $R^9$ and $R^{11}$ are each hydrogen.

The process of any previous embodiment, wherein $R^8$ and $R^{10}$ are each tert-butyl.

The process of any previous embodiment, wherein $E^1$ and $E^2$ are each O.

The process of any previous embodiment, wherein $E^1$ and $E^2$ are independently chosen from O and S.

The process of any previous embodiment, wherein $E^1$-$X^1$-$E^2$ is 3,5 dibutylcatecholate, and $R^1$—$X^2$—$R^2$ is 1,5-cyclooctadiene.

The process of any previous embodiment, wherein the unsaturated compound is chosen from an unsaturated polyether; an alkyl capped allyl polyether; a methylallyl polyether; a terminally unsaturated amine; an alkyne; a C2-C45 linear or branched olefin; an unsaturated epoxide; a terminally unsaturated acrylate; a terminally unsaturated methacrylate; a terminally unsaturated diene; an aliphatically unsaturated aryl ether; an aliphatically unsaturated aromatic hydrocarbon; an unsaturated cycloalkane; a vinyl-functionalized polymer or oligomer; a vinyl-functionalized and/or terminally unsaturated allyl-functionalized or alkenyl-functionalized silane or siloxane; an unsaturated fatty acid; an unsaturated fatty ester; an aliphatically unsaturated synthetic or natural mineral; or a combination of two or more thereof.

The process of any previous embodiment, wherein the unsaturated compound is chosen from polyoxyalkylenes having the general formula:

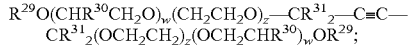

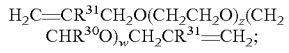

or a combination of two ore thereof, wherein $R^{28}$ is independently an unsaturated organic group containing from 2 to 10 carbon atoms; $R^{29}$ is independently hydrogen, an acyl group, or an alkyl group having from 1 to 8 carbon atoms; $R^{30}$ is independently a monovalent hydrocarbon group; $R^{31}$ independently chosen from hydrogen and a monovalent hydrocarbon group; each occurrence of z is 0 to 100 inclusive; and each occurrence of w is 0 to 100 inclusive.

The process of any previous embodiment, wherein the silylhydride is chosen from a compound of the formula $R^{12}{}_m SiH_p X_{4-(m+p)}$ and/or $M_a M^H{}_b D_c D^H{}_d T_e T^H{}_f Q_g$, where each $R^{12}$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M is a monofunctional group of formula $R^{13}{}_3 SiO_{1/2}$, D is a difunctional group of formula $R^{14}{}_2 SiO_{2/2}$, a T is a trifunctional group of formula $R^{15} SiO_{3/2}$, Q is a tetrafunctional group of formula $SiO_{4/2}$, $M^H$ is $HR^{16}{}_2 SiO_{1/2}$, $T^H$ represents $HSiO_{3/2}$, and $D^H$ is $R^{17} HSiO_{2/2}$; each occurrence of $R^{13-17}$ is independently C1-C18 alkyl, C1-C18 substituted alkyl, C6-C14 aryl or substituted aryl, wherein R10-14 optionally contains at least one heteroatom.

The process of any previous embodiment, wherein the silylhydride is a chlorosilane, $R^{12}{}_m SiH_p X_{4-(m+p)}$, $M_a D^H{}_d M_a$, where R12 is a C1-C10 alkoxy, m is 1-3, and p is 1-3, M is a monofunctional group of formula $R^{13}{}_3 SiO_{1/2}$, $D^H$ is $R^{17} HSiO_{2/2}$; each occurrence of $R^{13}$ and $R^{17}$ is independently C1-C18 alkyl, C1-C18 substituted alkyl, C6-C14 aryl or substituted aryl, wherein $R^{13}$ and $R^{17}$ optionally contains at least one heteroatom, and a and d are such that the molar mass of the silylhydride is between 100 and 100,000 Dalton.

The process of any previous embodiment, wherein the silylhydride is a compound of the formula $R^{18} R^{19} R^{20} Si(CH_2 R^{21})_x SiOSiR^{22} R^{23} (OSiR^{24} R^{25})_y OSiR^{26} R^{27} H$, where $R^{18}$-$R^{27}$ are independently chosen from hydrogen, a monovalent alkyl group, a cycloalkyl group, and an aryl group; x has a value of 1-8, and y has a value from zero to 10.

The process of any previous embodiment, where the unsaturated compound is allyl methacrylate.

The process of any previous embodiment, wherein the unsaturated compound is allyl glycidyl ether.

The process of any previous embodiment, where the unsaturated compound is an allyl or methallyl polyether.

The process of any previous embodiment, where the reaction is carried out at a temperature of −50° C. to 250° C.

The process of any previous embodiment, where the reaction is conducted in the presence of a solvent chosen from a hydrocarbon, a halogenated hydrocarbon, an ether, an alcohol, or a combination of two or more thereof.

The process of any previous embodiment, wherein the platinum concentration is from about 100 parts per billion to about 100 parts per million.

These and another aspects and embodiments are further understood with respect to the following detailed description.

DETAILED DESCRIPTION

The present invention is directed to a process for producing a hydrosilylated product comprising reacting a mixture comprising (a) compound containing at least one unsaturated group, (b) a silylhydride, and (c) a hydrosilylation catalyst, optionally in the presence of a solvent, in order to produce the hydrosilylated product. The hydrosilylation catalyst comprises a platinum-diene complex with chelating dianionic ligands. In one embodiment, the catalyst is a complex of the Formula (I) or an adduct thereof;

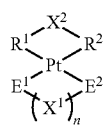

(I)

where $R^1-X^2-R^2$ is a diene that is bonded to platinum in an $\eta^4$-mode and is chosen from a branched or unbranched chain, a cyclic structure, or a bicyclic system having 4 to 30 carbon atoms, whereby the diene comprises bonding olefin moieties that are terminal and/or internal, and $X^2$ represents one or more bridges between the olefinic groups;

$E^1$ and $E^2$ are independently chosen from a mono-anionic group of O, $NR^3$, carboxyl group (C(O)O), and S; $R^3$ is independently hydrogen, or a monovalent hydrocarbon radical having from 1 to 30 carbon atoms;

$X^1$ is a divalent hydrocarbyl or silicone group chosen from a substituted or unsubstituted alkylene, an arylene, or a siloxanylene group;

$X^2$ is a divalent hydrocarbyl group chosen from a substituted or unsubstituted alkylene, an arylene, or a cycloalkylene group; and n is 0, 1, 2, 3, or 4.

A wide variety of chelating $E^1-X^1-E^2$ ligands can be employed as co-ligands in Pt (II) diene cure catalysts. Not to be bound by any particular theory or mechanism, desirable $E^1-X^1-E^2$ ligands would impart good solubility to the platinum catalyst in silicone formulations or organic solvent, and the chelating ligand would be rapidly decomplexed/eliminated at elevated temperature (in the presence of a silylhydride). Chelating $E^1-X^1-E^2$ ligands useful in this invention include amidos, thiolates, alkoxides, carboxylates, or ligands containing one or more of these functional groups.

Examples of suitable dianionic chelating ligands include, but are not limited to, amidophenolate, phenylenediamide, benzenedithiolate, mercaptophenolate, mercaptoethanolate, pinacolate, ethane diolate, propanediolate, catecholate, substituted catecholates, salicylate, oxalate, malonate, N,O-dianions of amino acids, etc.

In embodiments, the dianionic chelating ligand $E^1-X^1-E^2$ is represented by the formula:

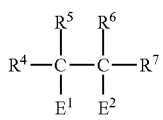

(II)

where $R^4$, $R^5$, $R^6$, and $R^7$ are independently chosen from hydrogen, a C1-C20 alkyl, and a C6-C10 aryl, and $E^1$ and $E^2$ may be as previously described. In embodiments, $R^4-R^7$ are independently chosen from a C1-20 alkyl including, but not limited to, methyl, ethyl, propyl, isopropyl, butyl, isobutyl, tert-butyl, pentyl, hexyl, etc.

In embodiments, the dianionic chelating ligand $E^1-X^1-E^2$ is represented by the formula:

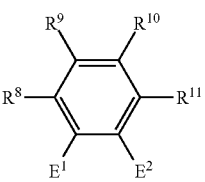

(III)

where $R^8$, $R^9$, $R^{10}$, and $R^{11}$ are independently chosen from hydrogen and a C1-C20 alkyl, and $E^1$ and $E^2$ may be as previously described. In embodiments, $R^8-R^{11}$ are independently chosen from hydrogen and a C1-C10 alkyl, even a C1-C6 alkyl. Examples of suitable alkyl groups for $R^8-R^{11}$ include but are not limited to, methyl, ethyl, propyl, isopropyl, butyl, isobutyl, tert-butyl, pentyl, hexyl, etc. In one embodiment, $R^8$ and $R^{10}$ are a C1-C10 alkyl, and $R^9$ and $R^{11}$ are each hydrogen. In one embodiment, $R^8$ and $R^{10}$ are each tert-butyl.

The $E^1$ and $E^2$ groups may be the same or different from one another in the dianionic chelating ligand. In embodiments, the $E^1$ and $E^2$ groups are each O. In other embodiments, $E^1$ is O, and $E^2$ is S.

The chelating diene compounds for $R^1-X^2-R^2$ are not particularly limited and can be chosen from a variety of diene compounds. Examples of suitable chelating dienes include, but are not limited to, 1,3-butadiene, isoprene, 2,3-dimethylbutadiene, 1,4-diphenyl-1,3-butadiene, 1,4-cyclohexadiene, 1,4-hexadiene, 2,4-hexadiene, 1,5-hexadiene, 1,5-cyclooctadiene, 1,5-dimethyl-1,5-cyclooctadiene, 1,6-dimethyl-1,5-cyclooctadiene, 1,3 dodecadiene, norbornadiene, dicyclopentadiene, etc.

The silyl hydride and/or hydrosiloxane employed in the reactions is not particularly limited. It can be, for example, any compound chosen from hydrosilanes or hydrosiloxanes including those compounds of the formulas $R^{12}_m SiH_pX_{4-(m+p)}$ or $M_aM^H_bD_cD^H_dT_eT^H_fQ_g$, where each $R^{12}$ is independently a substituted or unsubstituted aliphatic or aromatic hydrocarbyl group, X is halide, alkoxy, acyloxy, or silazane, m is 1-3, p is 1-3, and M, D, T, and Q have their usual meaning in siloxane nomenclature, with the proviso that when X is halide, the unsaturated substrate is not an alkyne. In embodiments, X is chlorine. The subscripts a, b, c, d, e, f, and g are such that the molar mass of the siloxane-type reactant is between 100 and 100,000 Dalton. In one embodiment, an "M" group represents a monofunctional group of formula $R^{13}_3SiO_{1/2}$, a "D" group represents a difunctional group of formula $R^{14}_2SiO_{2/2}$, a "T" group represents a trifunctional group of formula $R^{15}SiO_{3/2}$, and a "Q" group represents a tetrafunctional group of formula $SiO_{4/2}$, an "$M^H$" group represents $HR^{16}_2SiO_{1/2}$, a "$T^H$" represents $HSiO_{3/2}$, and a "$D^H$" group represents $R^{17}HSiO_{2/2}$. Each occurrence of $R^{13-17}$ is independently C1-C18 alkyl, C1-C18 substituted alkyl, C6-C14 aryl or substituted aryl, wherein $R^{13-17}$ optionally contains at least one heteroatom. In embodiments, the hydrosiloxane is of the formula $M_aD^H_dM_a$, where M, D, a, and d, are as described above. In other embodiments, the silyl hydride is such that $R^{12}$ is a C1-C10 alkoxy, and m is 1-3. In embodiments, $R^{12}$ is a C1-C10 alkoxy, and m is 1.

The instant invention also provides hydrosilylation with hydridosiloxanes comprising carbosiloxane linkages (for example, Si—CH$_2$—Si—O—SiH, Si—CH$_2$—CH$_2$—Si—O—SiH or Si-arylene-Si—O—SiH). Carbosiloxanes contain both the —Si-(hydrocarbylene)-Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. Nos. 7,259,220; 7,326,761 and 7,507,775 all of which are incorporated herein in their entirety by reference. An exemplary formula for hydridosiloxanes with carbosiloxane linkages is $R^{18}R^{19}R^{20}Si(CH_2R^{21})_x SiOSiR^{22}R^{23}(OSiR^{24}R^{25})_y OSiR^{26}R^{27}H$, wherein $R^{18}$-$R^{27}$ is independently a monovalent alkyl, cycloalkyl or aryl group such as methyl, ethyl, cyclohexyl or phenyl. Additionally, $R^{15-24}$ independently may also be H. The subscript x has a value of 1-8, y has a value from zero to 10 and is preferably zero to 4. A specific example of a hydridocarbosiloxane is $(CH_3)_3SiCH_2CH_2Si(CH_3)_2OSi(CH_3)_2H$.

As used herein, "unsaturated" refers to a compound comprising one or more double or triple bonds. In one embodiment, unsaturated refers to a compound comprising carbon-carbon double or triple bonds. The unsaturated compound containing at least one unsaturated functional group employed in the hydrosilylation reaction is generally not limited and can be chosen from an unsaturated compound as desired for a particular purpose or intended application. The unsaturated compound can be a mono-unsaturated compound or it can comprise two or more unsaturated functional groups. In one embodiment, the unsaturated group can be an aliphatically unsaturated functional group. Examples of suitable compounds containing an unsaturated group include, but are not limited to, unsaturated polyethers such as alkyl-capped allyl polyethers, vinyl functionalized allyl or methylallyl polyethers; terminally unsaturated amines; alkynes (except with hydrochlorosilanes); C2-C45 linear or branched olefins, in one embodiment alpha olefins; terminally unsaturated dienes; unsaturated epoxides such as allyl glycidyl ether and vinyl cyclohexene-oxide; terminally unsaturated acrylates or methacrylates; unsaturated aryl ethers; aliphatically unsaturated aromatic hydrocarbons; unsaturated cycloalkanes such as trivinyl cyclohexane; vinyl-functionalized polymer or oligomer; vinyl-functionalized and/or terminally unsaturated allyl-functionalized silane and/or vinyl-functionalized silicones; unsaturated fatty acids; unsaturated fatty esters; or combinations of two or more thereof. Illustrative examples of such unsaturated substrates include, but are not limited to, ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate-or acrylate prepolymers, polybutadiene, allylamine, methallyl amine, methyl undecenoate, acetylene, phenylacetylene, vinyl-pendent or vinyl-terminal polysiloxanes, vinylcyclosiloxanes, vinylsiloxane resins, other terminally-unsaturated alkenyl silanes or siloxanes, vinyl-functional synthetic or natural minerals, etc.

Unsaturated polyethers suitable for the hydrosilylation reaction include polyoxyalkylenes having the general formula:

$$R^{28}(OCH_2CH_2)_z(OCH_2CHR^{30})_w\text{—}OR^{29} \quad \text{(Formula IV); or}$$

$$R^{29}O(CHR^{30}CH_2O)_w(CH_2CH_2O)_z\text{—}CR^{31}_2\text{—}C\equiv C\text{—}CR^{31}_2\text{—}(OCH_2CH_2)_z(OCH_2CHR^{30})O_wR^{29} \quad \text{(Formula V); or}$$

$$H_2C=CR^{31}CH_2O(CH_2CH_2O)_z(CH_2CHR^{30}O)_wCH_2CR^{31}=CH_2 \quad \text{(Formula VI)}$$

wherein $R^{28}$ denotes an unsaturated organic group containing from 2 to 10 carbon atoms such as vinyl, allyl, methallyl, propargyl or 3-pentynyl. When the unsaturation is olefinic, it is desirably terminal to facilitate smooth hydrosilylation. However, when the unsaturation is a triple bond, it may be internal. $R^{29}$ is independently hydrogen, an alkyl group, e.g., from 1 to 8 carbon atoms such as the alkyl groups $CH_3$, $n$-$C_4H_9$, $t$-$C_4H_9$ or $i$-$C_8H_{17}$, and an acyl group, e.g., $CH_3COO$, $t$-$C_4H_9COO$, the beta-ketoester group such as $CH_3C(O)CH_2C(O)O$, or a trialkylsilyl group. $R^{30}$ and $R^{31}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^{31}$ may also be hydrogen. Methyl is the most preferred $R^{30}$ and $R^{31}$ groups. Each occurrence of z is 0 to 100 inclusive and each occurrence of w is 0 to 100 inclusive. Preferred values of z and w are 1 to 50 inclusive.

The present process can also be used, for example, for preparing a silylated polyurethane. This may include the step of contacting a terminally-unsaturated polyurethane with a silylhydride in the present of a platinum catalyst.

The concentration of platinum catalyst used in the present process can be varied. In one embodiment, the concentration of platinum is from about 100 parts per billion (ppb) to about 100 ppm; from about 500 ppb to about 70 ppm; from about 1 ppm to about 50 ppm; even from about 10 ppm to about 30 ppm. In embodiments, the platinum concentration is from about 0.5 ppm to about 10 ppm; from about 1 ppm to about 7.5 ppm; even from about 2 ppm to about 5 ppm. Here as elsewhere in the specification and claims, numerical values can be combined to form new and alternative ranges.

The platinum catalyst may be dissolved in solvent to improve ease of handling. The solvent is not limited and can be either polar or non-polar. Any solvent can be used in the method of the invention, as long as it facilitates the dissolution of the platinum catalyst, without deleterious effects.

The temperature range for the process of the hydrosilylation is from −50° C. to 250° C., preferably from 0° C. to 150° C. A variety of reactors can be used in the process of this invention. The process can be run as a batch reaction or a continuous reaction at ambient, sub-ambient, or supra-ambient pressures. In one embodiment, the reaction is carried out under an inert atmosphere. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated or hydrosilylated reaction product. With gaseous or volatile olefins and silanes, fluidized-bed reactors, fixed-bed reactors and autoclave reactors can be more appropriate.

Accordingly, in some embodiments, the present invention is also directed to the compositions produced from the above described methods. These compositions contain the hydrosilylated products of the silylhydride and the compound having at least one unsaturated group. The hydrosilylated products that are produced by the process of the present invention have uses in the synthesis of silicone materials such as organosilanes for coupling agents, adhesives, products for agricultural and personal care applications, and silicone surfactant for stabilizing polyurethane foams.

The following examples are intended to illustrate, but in no way limit the scope of the present invention. All parts and percentages are by weight and all temperatures are in Celsius unless explicitly stated otherwise. All patents, other publications, and U.S. patent applications referred to in the instant application are incorporated herein by reference in their entireties.

EXAMPLES

Experimental

Reactions and manipulations were performed under nitrogen, using standard Schienk-line techniques. The preparation of the platinum complexes was performed according to published procedures for $^tBu_2$—$C_6H_2O_2$PtCOD (Boyer et al. Inorg. Chem 2009, 48, 638-645.) and $C_6H_4S_2$PtCOD (Rath et at Inorg. Chim. Acta, 2007, 306(5), 1767-1770.) The $^1H$, $^{13}C$ and $^{29}Si$ NMR spectra were recorded on a Bruker 200 mHZ and 400 mHz spectrometers. GC analysis was performed using an Aligent 7890A gas chromatograph. The following abbreviations and terms are used: THF, tetrahydrofuran; NMR, Nuclear Magnetic Resonance. The Hazen values were obtained with a BYK liquid color meter.

3,5-$^tBu_2$-c atecholatePtCOD: A flask was charged with 3,5-ditertbutylcatechol (0.21 g, 1 mmol) and potassium tertbutoxide (0.22 g, 2 mmol). The flask was purged with $N_2$. The material was dissolved in 30 mL of dry THF. A second flask was charged with PtCODCl$_2$ (0.35 g, 1 mmol). The flask was purged with $N_2$. The PtCODCl$_2$ was dissolved in 60 mL of $CH_2Cl_2$. The deprotonated catechol was added to the PtCODCl$_2$ solution via cannula. Immediately a dark orange solution formed and a white precipitate. The material was stirred for 3 hours. The material was filtered to remove the white solid. The orange filtrate was concentrated under vacuum. The product was extracted in DCM/hexanes (60 mL, 2:1). Obtained 0.44 g orange solid (90% yield). Obtained 0.44 g orange solid (90% yield). $^1H$ NMR (CDCl$_3$): 6.78 (s, 1H, aryl), 6.64 (s, 1H, aryl), 5.31 (m, $J_{Pt-H}$=77 Hz, 4H, CH), 2.64 (bs, 4H, CH$_2$), 2.30 (bs, 4H, CH$_2$), 1.38 (s, 9H, $^tBu$), 1.27 (s, 9H, $^tBu$). $^{13}C$ NMR (CDCl$_3$): 160.9 (C=O), 157.6 (C=O), 140.5 (C$_{aryl}$), 135.0 (J$_{C-Pt}$=53.7 Hz, C$_{aryl}$), 112.5 (CH$_{aryl}$), 110.5 (J$_{Pt-C}$=61.6 Hz, CH$_{aryl}$), 87.1 (J$_{Pt-C}$=173.8 Hz, C$\alpha$C), 32.1 (C$^4$Bu), 30.0 ($^tBu$), 29.8 ($^tBu$), 29.7 (CH$_2$). $^{195}$Pt NMR (CDCl$_3$): −3210.

PinacolatePtCOD: A dry round bottomed flask was charged with 2,3-dimethyl-2,3-butanediol (1.2 g, 10.2 mmol), under nitrogen, and anhydrous THF (30 mL) was added. A separate schlenk flask was charged with potassium tert-butoxide (2.2 g, 20 mmol) under a nitrogen atmosphere and dissolved in anhydrous THF (30 mL). A separate round bottom was charged with a solution of PtCODCl$_2$ (3.6 g, 9.7 mmol) in dichloromethane (150 mL), and placed under nitrogen atmosphere. The 2,3-dimethyl-2,3-butanediol solution was transferred via cannula to the potassium tert-butoxide solution. The cloudy mixture was allowed to stir for 5 min before being transferred via cannula to the PtCODCl$_2$ solution. This yielded a yellow solution that slowly darkened as it stirred under nitrogen at room temperature. After 4 hours the slightly cloudy solution was stopped stirring and filtered through filter paper. The filtrate was reduced under vacuum to a brown solid. The isolated brown solid was dissolved in 25 mL of dichloromethane and diluted with 250 mL of heptanes. A brown ppt formed and was filtered off, the filtrate was reduced to obtain 3.2 g of a tan solid (79% yield). $^1H$ NMR (CDCl$_3$): 4.83 (bs, $J_{Pt-H}$=61.6 Hz, 4H, CH), 2.53 (m, 4 H, CH$_2$), 2.15 (m, 4 H, CH$_2$), 1.21 (s, 12 H, CH$_3$). $^{13}C$ NMR (CDCl$_3$): 88.2 (J$_{Pt-C}$=164.5 Hz, C=C), 86.4 (CO), 30.0 (CH$_2$), 27.2 (J$_{Pt-C}$=20.5, CH$_3$). $^{195}$Pt NMR (CDCl$_3$): −3180.

C$_6$H$_4$ONMePtCOD: This material was prepared similar to 3,5-$^tBu_2$-catecholatePtCOD except the material was extracted into diethyl ether. The solvent was removed under vacuum to afford an orange solid. Yield 81%. $^1H$ NMR (CDCl$_3$): 6.5-6.9 ppm (m, 4H, aryl), 5.22 (bs, J$_{Pt-H}$=54 Hz, 2H, CH), 4.03 (bs, J$_{Pt-H}$=65 Hz, 2H, CH), 3.19 (s, J$_{Pt-H}$=30 Hz, 3H, N-Me), 2.2-2.8 (m, 8H, CH$_2$). $^{13}C$ NMR (CDCl$_3$): 161.4 (C=O), 151.8 (J$_{Pt-C}$=44.8 Hz, C=N), 118.2 (CH$_{aryl}$), 116.6 (CH$_{aryl}$), 113.4 (J$_{Pt-C}$=59.6 Hz, CH$_{aryl}$), 108.7 (J$_{Pt-C}$=39 Hz, CH$_{aryl}$), 88.9 (J$_{Pt-C}$=148.1, C=C), 84.3(J$_{Pt-C}$=188.6, C=C), 36.7 (J$_{Pt-C}$=56.9 Hz, N-Me), 31.1 (CH$_2$), 29.2 (CH$_2$). $^{195}$Pt NMR (CDCl$_3$): −3498 ppm.

C$_6$H$_4$(NMe)$_2$PtCOD: This material was prepared similar to 3,5-$^tBu_2$-catecholatePtCOD except the material was extracted into diethyl ether. The solvent was removed under vacuum. The brown tacky residue was recrystallized from DCM/pentane. Obtained 38% yield of a dark brown microcrystalline material. $^1H$ NMR (CDCl$_3$): 6.67-6.86 (m, 4H, aryl), 4.79 (bs, 4H, J$_{Pt-H}$=54.7 Hz, CH), 3.32 (bs, 6H, J$_{Pt-H}$=29.7 Hz, N-Me), 2.33-2.76 (m, 8H, CH$_2$). $^{13}C$ NMR (CDCl$_3$): 150.0 (J$_{Pt-C}$=40.7 Hz, C=N), 116.1 (CH$_{aryl}$), 106.8 (J$_{Pt-C}$=40.5 Hz, CH$_{aryl}$), 83.1 (J$_{Pt-C}$=162.Hz, C=C), 36.9 (J$_{Pt-C}$=46.4 Hz, N-Me), 30.4 (CH$_2$). $^{195}$Pt NMR (CDCl$_3$): −3828 ppm.

C$_6$H$_4$SOPtCOD: This material was prepared in a similar manner to 3,5-$^tBu_2$-catecholatePtCOD. Orange solid. Yield 73%. $^1H$ NMR (CDCl$_3$): 7.37 (d, J=7.5 Hz, 1H, aryl), 6.87 (m, 2H, aryl), 6.67 (m, 1 H, aryl), 5.69 (bs, J$_{Pt-H}$=54.1 Hz, 2H, CH), 5.69 (bs, J$_{Pt-H}$=61.6 Hz, 2H, CH), 2.63 (m, 4 H, CH$_2$), 2.39 (m, 4H, CH$_2$). $^{13}C$ NMR (CDCl$_3$): 171.1 (C=S), 130.8 (C=S),(127.9 (J$_{Pt-C}$=54.25 Hz, CH$_{aryl}$), 124.2 (CH$_{aryl}$), 118.5 (CH$_{aryl}$), 116.1 (J$_{Pt-C}$=78.92 Hz, CH$_{aryl}$), 100.6 (J$_{Pt-C}$=113.4 Hz, C=C), 79.8 (J$_{C-Pt}$=174.61 Hz, C=C), 31.3 (CH$_2$), 28.9 (CH$_2$). $^{195}$Pt NMR (CDCl$_3$): −3583.

SalicylatePtCOD: This material was prepared in a similar manner to 3,5-$^tBu_2$-catecholatePtCOD with the following exceptions. The PtCODCl$_2$ solution was added to the stirring solution of salicylic acid and KO$^t$Bu in THF. The isolated material was washed with toluene isolating a yellow solid. Yield 46%. $^1H$ NMR (CDCl$_3$): 8.12 (dd, J=8.3 Hz, J=1.6 Hz 1H, aryl), 7.25 (td, J=7.5 Hz, J=1.5 Hz 1H, aryl), 6.80 (t, J=7.5 Hz, aryl), 6.72 (d, J=8.3 Hz, 1H, aryl), 5.36 (bs, J$_{Pt-H}$=66.0 Hz, 4H, CH), 2.76 (m, 4 H, CH$_2$), 2.32 (m, 4 H, CH$_2$). $^{13}C$ NMR (CDCl$_3$): 165.7 (OCO), 164.7 (C$_{Ph}$), 133.1 (C$_{Ph}$), 132.7 (C$_{Ph}$), 119.5 (J$_{Pt-C}$=50.8 Hz, C$_{Ph}$), 118.1 (C$_{Ph}$), 117.6 (C$_{Ph}$O), 95 (J$_{Pt-C}$=168.9 Hz, C=C), 94.9 (J$_{Pt-C}$=184.9 Hz, C=C), 29.8 (CH$_2$), 29.7 (CH$_2$). $^{195}$Pt NMR (CDCl$_3$): −2899.

Example 1

Hydrosilylation of Allyl Polyoxyethylene (APEG) with MD$^H$M Using (3,5-$^tBu_2$catecholate)PtCOD as a Catalyst A 4-neck round bottomed flask was equipped with a magnetic stir bar. A water condenser fitted with a dry ice condenser was attached to the central neck. A liquid addition funnel was attached to another neck. The remaining 2 necks were stoppered with a ground glass stopper and rubber septa. A J-Kem temperature probe connected to a heating mantle and was introduced through the rubber septum. The addition funnel was equipped with a $N_2$ inlet and the $N_2$ line was split with a t-piece attached to a bubbler. The entire set-up was inerted with $N_2$. The reaction vessel was charged with APEG350R (35.3 g, 0. 0.086 mol, 1.3 eq), 20% of the total volume of $MD^HM$ (2.96 g, 0.013 mol, 0.2 eq) and sodium propionate (18 mg, 360 ppm). The liquid addition funnel was charged with the remainder of the $MD^HM$ (11.74 g, 0.053 mol, 0.8 eq). The reaction vessel was heated to the set temperature of 90° C. under $N_2$ with constant stirring. A 0.15 wt % catalyst solution of (3,5 $^t$Butyl catecholate)PtCOD (200 μL, 2 ppm Pt w/w) in xylenes was quickly injected via syringe to the reaction mixture. After confirmation of a reaction exotherm, the remainder of the $MD^HM$ was added via addition funnel at a rate aimed to complete the addition in 30 minutes. After final addition of the $MD^HM$, the temperature was maintained at 90° C. for up to 4 hours during which the reaction mixture was monitored by hydride testing at regular intervals to check for completion of the reaction. The product was analyzed by NMR for residual APEG and its internal isomers. The Hazen value and viscosity of the product was also measured. A similar procedure was followed with other Pt-COD except were differences were noted in the table.

Comparative Example 1

Hydrosilylation of Allyl Polyoxyethylene (APEG) with $MD^HM$ Using Chloroplatinic Acid (CPA) as a Catalyst A reaction was run similarly as in Example 1 except that a 3.2 wt % chloroplatinic acid (CPA) solution in ethanol was used as catalyst. Table A lists the time to completion, final hydride content and hydride content after 15 minutes of completion of addition of $MD^HM$.

Example 2

Hydrosilylation of Octene with Triethoxysilane Using (3,5 $^t$Bu$_2$ catecholate)PtCOD as a Catalyst All glassware was dried in an oven at 125° C. overnight prior to use. A 4 neck round bottom flask was fitted with an addition funnel, two rubber septa, a magnetic stir bar, and a water condenser fitted with a dry ice condenser. The addition funnel was equipped with a $N_2$ inlet and the $N_2$ line was split with a t-piece attached to a bubbler whose exit was passed through a scrubber filled with a KOH/ethanol solution. A J-Kem temperature probe connected to a heating mantle and was introduced through one rubber septum. The set-up was purged with $N_2$ flow, and the 4-neck round bottom was charged with 1-octene (36.6 mL, 0.229 mol) and was blanketed with $N_2$. An amount of triethoxysilane (39.0 mL, 0.207 mol), was added to the addition funnel and purged with $N_2$. An additional 2 mL (0.01 mol) of triethoxysilane was added to the 1-octene in the round bottom. The mixture in the round bottom was heated to 70° C., at which time glacial acetic acid (0.038 g) was added to the mixture. At 70° C., a solution of (3,5 tBu$_2$-catecholate)PtCOD was added (1.61 $E^{-07}$ mol Pt, 0.5 ppm Pt) and the reaction was monitored for exotherm. Upon confirmation of the exotherm, the reaction was closely monitored and kept below 80° C. while triethoxysilane was added. The triethoxysilane was added over 45 minutes after which the reaction was allowed to stir at 70° C. for 90 minutes sampling for GC analysis at the 0, 15, 30, 60 minute marks. At the end of 90 minutes the reaction was sampled for GC analysis, removed from heat, and was cooled to room temperature. The final product was shown to be 88.8% product via GC and had a Hazen value of 6.

Comparative Example 2

Hydrosilylation of Octene with Triethoxysilane Using Karstedt's Catalyst

A reaction was run as above with respect to Example 2 but with the addition of Karstedt's Catalyst (1.61 $E^{-07}$ mol Pt, 0.5 ppm Pt) in place of the (3,5 tBu$_2$-catecholate)PtCOD complex. The triethoxysilane was added over 45 minutes after which the reaction was allowed to stir at 70° C. for 90 minutes sampling for GC analysis at the 0, 15, 30, 60 minute marks. At the end of 90 minutes the reaction was sampled for GC analysis, removed from heat, and was cooled to room temperature. The final product was shown to be 51.8% product via GC and had a Hazen value of 32.

Example 3

Hydrosilylation of Allyl Glycidyl Ether with Tri-ethoxysilane Using 3,5-$^t$Bu$_2$catecholatePtCOD as a Catalyst All glassware was dried in an oven at 125° C., overnight, prior to use. A 4 neck round bottom flask was fitted with an addition funnel, two rubber septa, a magnetic stir bar, and a water condenser fitted with a dry ice condenser. The addition funnel was equipped with a $N_2$ inlet and the $N_2$ line was split with a t-piece attached to a bubbler whose exit was passed through a scrubber filled with a KOH/ethanol solution (to quench any $SiH_4$ formed). A J-Kem temperature probe connected to a heating mantle and was introduced through one rubber septum. The set-up was purged with $N_2$ flow, and the 4-neck round bottom was charged with allyl glycidyl ether (AGE, 33.3 mL, 0.281 mol) and was blanketed with $N_2$. An amount of triethoxysilane (45.0 mL, 0.240 mol), was added to the addition funnel and purged with $N_2$. The material in the round bottom was heated to 90° C., at which time glacial acetic acid (0.17 g) was added to the mixture. As the temperature equilibrated to 70° C. a solution of (3,5$^2$13u$_2$-catecholate)PtCOD was added (1.12 $E^{-06}$ mol Pt, 3.0 ppm Pt) and the reaction was monitored for exotherm. Upon confirmation of the exotherm, the reaction was closely monitored and kept below 100° C. while triethoxysilane was added. The triethoxysilane was added over 38 minutes after which the reaction was allowed to stir at 90° C. for 120 minutes sampling for GC analysis at the 0, 15, 60 minute marks. At the end of 120 minutes the reaction was sampled for GC analysis, removed from heat, and was cooled to room temperature.

Comparative Example 3

Hydrosilylation of Allyl Glycidyl Ether with Triethoxysilane Using Chloroplatinic Acid as a Catalyst The reaction was run as above in Example 3 but with the addition of chloroplatinic acid (1.12 $E^{-06}$ mol Pt, 3.0 ppm Pt) in place of the (3,5$^2$Bu$_2$-catecholate)PtCOD complex. The triethoxysilane was added over 39 minutes after which the reaction was allowed to stir at 90° C. for 120 minutes sampling for GC analysis at the 0, 15, 60 minute marks. At the end of 120 minutes the reaction was sampled for GC analysis, removed from heat, and was cooled to room temperature.

TABLE 1

Reaction Conditions and results for the hydrosilylation of APEG with MD$^H$M with various Pt complexes at 2 ppm Pt loading.

| Catalyst | $t_{(completion)}$ (mins) | $H_2$ 15 min (mL/g) | $H_2$ final (mL/g) |
|---|---|---|---|
| CPA-A | 55 | 2.62 | 0 |
| CPA-A | 120 | 7.85 | 0.11 |
| CPA-A | 75 | 3.86 | 0 |
| CPA-B | 120 | 4.6 | 0 |
| CPA-B | 120 | 6.8 | 0 |
| Pt(3,5-$^t$Bu$_2$catecholate)COD-A | 47 | 5.8 | 0 |
| Pt(3,5-$^t$Bu$_2$catecholate)COD-A | 35 | 4.7 | 0 |
| Pt(3,5-$^t$Bu$_2$catecholate)COD-A | 55 | 4.3 | 0 |
| Pt(3,5-$^t$Bu$_2$catecholate)COD-B | 35 | 4.3 | 0.13 |
| Pt(3,5-$^t$Bu$_2$catecholate)COD-B | 55 | 4.5 | 0.06 |
| Pt(3,5-$^t$Bu$_2$catecholate)COD-C | 35 | 2.5 | 0 |
| Pt(3,5-$^t$Bu$_2$catecholate)COD-C | 35 | 2.1 | 0 |
| Pt(pinacolate)COD-A | 205 | 5.98 | 0 |
| Pt(pinacolate)COD-A | 55 | 2.6 | 0 |
| Pt(pinacolate)COD-A | 120 | 4.3 | 0.06 |
| Pt(mercaptophenolate)COD-A | 90 | 8.2 | 0 |
| Pt(α-hydroxy butyrate)COD-A | >4 hrs | 9.5 | 1.34 |
| Pt(salicylate)COD-C | 3 hrs | 6.9 | 0.07 |

A-Catalyst added at 90° C.;
B-Catalyst addition at room temperature and then heated to 90° C.
C-PtCODXY complex prepared in EtOH
Some runs were done in duplicate and triplicate.

TABLE 2

Reaction Conditions and results for the hydrosilylation of APEG with MD$^H$M with various Pt complexes at 120° C. and 2 ppm Pt loading.

| Catalyst | T (° C.) | $t_{(completion)}$ (mins) | $H_2$ 15 min (mL/g) | $H_2$ final (mL/g) | Hazen (Pt/Co) |
|---|---|---|---|---|---|
| chloroplatinic acid | 120 | 55 | 3.45 | 0 | 69 |
| Pt(3,5-$^t$Bu$_2$-catecholate)COD | 120 | 30 | 0.33 | 0 | 33 |

Tables 1 and 2 illustrate that the present catalysts are comparable to or perform better than conventional catalysts such as chloroplatinic acid in catalyzing hydrosilylation reactions. Several of the catalysts provide for faster reactions compared to chloroplatinic acid. Additionally, the present catalysts can provide a product having a lower yellowing index as indicated by the lower Hazen value.

Tables 3 and 4 compare the reaction of 1-octene with triethoxysilane over time using 3,5-$^t$Bu$_2$catecholatePtCOD (Table 3) or Karstedt's catalyst (Table 4). Tables 5 and 6 compare the reaction of allyl glycidyl ether with triethoxysilane over time using 3,5-$^t$Bu$_2$catecholatePtCOD (Table 5) or CPA as catalyst (Table 6).

TABLE 3

GC data for hydrosilylation reactions of 1-octene with triethoxysilane using 3,5-$^t$Bu$_2$catecholatePtCOD as a catalyst.

| Time (minutes) | 1-octene | octene isomers | TrES | TEOS | product |
|---|---|---|---|---|---|
| 0 | 37.68 | 2.02 | 21.24 | — | 39.06 |
| 15 | 35.95 | 2.14 | 21.15 | — | 40.77 |
| 30 | 22.34 | 2.91 | 13.46 | — | 61.3 |
| 60 | 8.2 | 4.00 | 5.34 | — | 82.46 |
| 90 | 3.68 | 4.31 | 2.85 | 0.33 | 88.83 |

TrES = Si(OEt)$_3$H
TEOS = Si(OEt)$_4$.

TABLE 4

GC data for the hydrosilylation reaction of 1-octene with triethoxysilane using Karstedt's catalyst.

| Time (minutes) | 1-octene | Octene isomers | TrES | TEOS | product |
|---|---|---|---|---|---|
| 0 | 58.8 | 1.11 | 34.43 | — | 5.66 |
| 15 | 57.99 | 1.05 | 34.46 | — | 6.49 |
| 30 | 56.59 | 1.05 | 34.01 | — | 8.35 |
| 60 | 40.17 | 1.85 | 24.17 | — | 33.82 |
| 90 | 28.21 | 2.67 | 17.31 | — | 51.82 |

TABLE 5

GC data for the hydrosilylation reaction of allyl glycidyl ether with triethoxysilane using 3,5-$^t$Bu$_2$catecholatePtCOD as a catalyst.

| Time (minutes) | AGE | AGE isomers | TrES | TEOS | product |
|---|---|---|---|---|---|
| 0 | 1.39 | 8.55 | 3.90 | — | 85.48 |
| 15 | — | 8.68 | 2.40 | 1.12 | 87.76 |
| 60 | — | 8.79 | 2.35 | 1.27 | 87.57 |
| 120 | — | 8.62 | 1.91 | 1.48 | 87.98 |

TABLE 6

GC data for the hydrosilylation reaction of allyl glycidyl ether with triethoxysilane using CPA as a catalyst.

| Time (minutes) | AGE | AGE isomers | TrES | TEOS | product |
|---|---|---|---|---|---|
| 0 | 19.84 | 5.41 | 19.86 | — | 54.89 |
| 15 | 12.96 | 6.28 | 13.36 | 0.88 | 66.51 |
| 60 | 2.04 | 7.99 | 2.80 | 1.15 | 86.02 |
| 120 | 0.41067 | 8.52 | 0.88 | 1.15 | 89.04 |

The results in Table 3 and 4 and those from Tables 5 and 6 show that reactions with Pt(3,5-tBu2-catecholate)(COD) reached completion faster than those done with CPA or Karstedt's catalyst.

Example 4

Hydrosilylation of Allyl Methacrylate (AMA) with Dimethylchlorosilane Using (3,5 $^t$Butyl Catecholate)PtCOD All glassware was dried in the oven prior to use. A 4-neck round bottomed flask was equipped with a magnetic stir bar. A water condenser fitted with a dry ice condenser was attached to the central neck. A liquid addition funnel was attached to another neck. The remaining 2 necks were stoppered with syringe ports sealed with Teflon septa. A J-Kem temperature probe connected to a heating mantle and was introduced through one of the syringe ports. The addition funnel was equipped with a $N_2$ inlet and the $N_2$ line was split with a t-piece to attached to a bubbler. The entire set-up was inerted with Ni. The reaction vessel was charged with the appropriate inhibitors and AMA (29.9 g, 0.237 mol, 1.12 eq). The liquid addition funnel was charged with dimethylchlorosilane (20.1 g, 0.212 mol, 1.0 eq). Additional tubing was fitted to the addition funnel to facilitate sub-surface addition. The reaction vessel was heated to the set temperature under $N_2$ with constant stirring. A 0.15 wt % catalyst solution of (3,5 $^t$Butyl catecholate)PtCOD (50 μL, 0.5 ppm Pt) in xylenes was quickly injected via syringe to the reaction mixture. A few drops (approximately 2 mL) of dimethylchlorosilane was added to the reaction vessel. The initial exotherm from the hydrosilylation reaction was controlled below 100° C. The remaining dimethylchlorosilane was added in 20-25 minutes with the temperature never exceeding 100° C. After completing the addition of dimethylchlorosilane, additional inhibitors were added. The reaction mixture was cooked at 85° C. and monitored for completion at regular intervals by GC. The reaction was cooled down to room temperature when no significant change in the AMA peak area was observed. The Hazen value of the product was also measured.

Comparative Example 4

Hydrosilylation of Allyl Methacrylate (AMA) with Dimethylchlorosilane Using Karstedt's Catalyst (K)

A reaction was run similarly as in Example 4 except that Karstedt's catalyst (1.31 E$^{-07}$ mol Pt, 0.5 ppm Pt) was used as catalyst.

TABLE 7

Reaction Conditions and results for the hydrosilylation of AMA with dimethylchlorosilane with various Pt complexes at 0.5 ppm Pt loading.

| Catalyst | $t_{initiation}$ (mins) | $t_{completion}$ (mins) | T (° C.) | GC (% peak area) | | | | | | Hazen |
|---|---|---|---|---|---|---|---|---|---|---|
| | | | | $t_0$ AMA | $t_{60}$ AMA | $t_0$ Me$_2$HSiCl | $t_{60}$ Me$_2$HSiCl | $t_0$ product | $t_{60}$ product | |
| Karstedt's* | >50 | | 85 | | | | | | | |
| Pt(cat)COD | 25 | 0 | 85 | 14.9 | 12.2 | 0.9 | 0 | 71.4 | 74.2 | 17 |
| Karstedt's | 25 | 15 | 90 | 20.4 | 12 | 2.6 | 0 | 65.5 | 73.6 | 16 |
| Pt(cat)COD | 25 | 15 | 90 | 15.9 | 11.9 | 1.24 | 0 | 69.9 | 72.9 | 18 |

*Reaction did not initiate after 40 minutes

In table 7, $t_{initiation}$ is the time taken for the initial exotherm to be observed. The reaction was deemed complete when ≤0.1 peak area % the dimethylchlorosilane (Me$_2$HSiCl) peak was detected by GC and is reported as $t_{completion}$. The data points $t_0$ and $t_{60}$ correspond to the sampling times in minutes starting from the time to complete the addition of dimethylchlorosilane. At 0.5 ppm Pt loading, the 3,5-$^t$Bu$_2$catecholatePtCOD catalyst (PtcatCOD) displayed a 25 minutes induction period. Karstedt's catalyst failed to initiate the reaction at 85° C. after 40 minutes of catalyst addition, but initiated in 25 minutes at 90° C. Though both Karstedt's and PtcatCOD complete the reaction in 15 minutes when run at 90° C., the PtcatCOD was found to have a greater conversion at $t_0$. The results in Table 7 show that (PtcatCOD) performs better than conventional catalysts such as Karstedt's in catalyzing hydrosilylation reactions involving chlorosilanes at 0.5 ppm Pt loading. No adverse effects like AMA isomerization or increased color were observed when PtcatCOD was used as a catalyst.

Embodiments of the invention have been described above and modifications and alterations may occur to others upon the reading and understanding of this specification. The claims as follows are intended to include all modifications and alterations insofar as they come within the scope of the claims or the equivalent thereof.

What is claimed is:

1. A process for the hydrosilylation of an unsaturated compound comprising reacting (a) a silyl hydride with (b) an unsaturated compound in the presence of (c) a hydrosilylation catalyst, optionally in the presence of a solvent, to produce a hydrosilylated product, wherein the hydrosilylation catalyst is a complex of Formula (I):

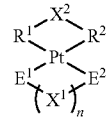

(I)

where $R^1$—$X^2$—$R^2$ is a diene that is bonded to platinum in an $\eta^4$-mode and is chosen from a branched or unbranched chain, a cyclic structure, or a bicyclic system having 4 to 30 carbon atoms, whereby $R^1$ and $R^2$ are olefinic groups comprising terminal and/or internal bonding olefin moieties, and $X^2$ is a divalent hydrocarbyl group chosen from an alkylene, an arylene, or a cycloalkylene group;

$E^1$ and $E^2$ are independently chosen from a mono-anionic group of O, NR$^3$ carboxyl group (C(O)O), and S; R$^3$ is independently hydrogen, or a monovalent hydrocarbon radical having from 1 to 30 carbon atoms;

$X^1$ is a divalent hydrocarbyl chosen from an alkylene, or an arylene; and n is 0, 1, 2, 3, or 4 with the proviso that $E^1$-$X^1$-$E^2$ is not an alpha hydroxy acid.

2. The process of claim 1, wherein $E^1$ and $E^2$ are O.

3. The process of claim 1, wherein $R^1$—$X^2$—$R^2$ is 1,5-cyclooctadiene.

4. The process of claim 1, wherein $E^1$-$X^1$-$E^2$ is chosen from an amidophenolate, a phenylenediamide, a benzenedithiolate, a mercaptophenolate, a mercaptoethanolate, a pinacolate, an ethylene diolate, a propandiolate, a catecholate, a catecholate, a salicylate, an oxalate, or malonate.

5. The process of claim 4, wherein $R^1$—$X^2$—$R^2$ is 1,5-cyclooctadiene.

6. The process of claim 4, wherein $E^1$-$X^1$-$E^2$ is chosen from:

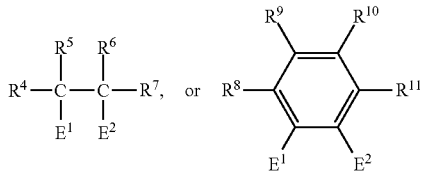

where $R^4$, $R^5$, $R^6$, and $R^7$ are independently chosen from hydrogen, a C1-C20 alkyl, and a C6-C10 aryl, and $R^8$, $R^9$, $R^{10}$, and $R^{11}$ are independently chosen from hydrogen and a C1-C20 alkyl.

7. The process of claim 6, wherein $R^8$, $R^9$, $R^{10}$, and $R^{11}$ are each hydrogen.

8. The process of claim 7, wherein $R^8$ and $R^{10}$ are independently chosen from a C1-C20 alkyl, and $R^9$ and $R^{11}$ are each hydrogen.

9. The process of claim 8, wherein $R^8$ and $R^{10}$ are each tert-butyl.

10. The process of claim 6, wherein $E^1$ and $E^2$ are each O.

11. The process of claim 6, wherein $E^1$ and $E^2$ are independently chosen from O and S.

12. The process of claim 1, wherein $E^1$-$X^1$-$E^2$ is 3,5-dibutylcatecholate, and $R^1$—$X^2$—$R^2$ is 1,5-cyclooctadiene.

13. The process of claim 1, wherein the unsaturated compound is chosen from an unsaturated polyether; an alkyl capped allyl polyether; a methylallyl polyether; a terminally unsaturated amine; an alkyne; a C2-C45 linear or branched olefin; an unsaturated epoxide; a terminally unsaturated acrylate; a terminally unsaturated methacrylate; a terminally unsaturated diene; an aliphatically unsaturated aryl ether; an aliphatically unsaturated aromatic hydrocarbon; an unsaturated cycloalkane; a vinyl-functionalized polymer or oligomer; a vinyl-functionalized and/or terminally unsaturated allyl-functionalized or alkenyl-functionalized silane or siloxane; an unsaturated fatty acid; an unsaturated fatty ester; or a combination of two or more thereof.

14. The process of claim 1, wherein the unsaturated compound is chosen from a polyoxyalkylene having the formula:

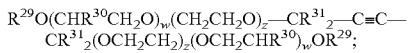

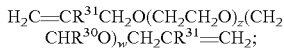

or a combination of two ore thereof, wherein $R^{28}$ is independently an unsaturated organic group containing from 2 to 10 carbon atoms; $R^{29}$ is independently hydrogen, an acyl group, or an alkyl group having from 1 to 8 carbon atoms; $R^{30}$ is independently a monovalent hydrocarbon group; $R^{31}$ independently chosen from hydrogen and a monovalent hydrocarbon group having 1-20 carbon atoms; each occurrence of z is 0 to 100 inclusive; and each occurrence of w is 0 to 100 inclusive.

15. The process of claim 1, wherein the silylhydride is chosen from a compound of the formula $R^{12}{}_m SiH_p X_{4-(m+p)}$ and/or $M_a M^H{}_b D_c D^H{}_d T_e T^H{}_f Q_g$, where each $R^{12}$ is independently an aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M is a monofunctional group of formula $R^{13}{}_3 SiO_{1/2}$, D is a difunctional group of formula $R^{14}{}_2 SiO_{2/2}$, a T is a trifunctional group of formula $R^{15} SiO_{3/2}$, Q is a tetrafunctional group of formula $SiO_{4/2}$, $M^H$ is $HR^{16}{}_2 SiO_{1/2}$, $T^H$ represents $HSiO_{3/2}$, and $D^H$ is $R^{17} HSiO_{2/2}$; each occurrence of $R^{13-17}$ is independently C1-C18 alkyl, C6-C14 aryl, wherein $R^{13-17}$ optionally contains at least one heteroatom.

16. The process according to claim 1, wherein the silylhydride is a chlorosilane, $R^{12}{}_m SiH_p X_{4-(m+p)}$, $M_a D^H{}_d M_a$, where R12 is a C1-C10 alkoxy, m is 1-3, and p is 1-3, M is a monofunctional group of formula $R^{13}{}_3 SiO_{1/2}$, $D^H$ is $R^{17} HSiO_{2/2}$; each occurrence of $R^{13}$ and $R^{17}$ is independently C1-C18 alkyl, C6-C14 aryl, wherein $R^{13}$ and $R^{17}$ optionally contains at least one heteroatom, and a and d are such that the molar mass of the silylhydride is between 100 and 100,000 Dalton.

17. The process of claim 1, wherein the silylhydride is a compound of the formula $R^{18} R^{19} R^{20} Si(CH_2 R^{21})_x SiOSiR^{22} R^{23} (OSiR^{24} R^{25})_y OSiR^{26} R^{27} H$, where $R^{18}$-$R^{27}$ are independently chosen from hydrogen, a monovalent alkyl group, a cycloalkyl group, and an aryl group; x has a value of 1-8, and y has a value from zero to 10.

18. The process according to claim 1 where the unsaturated compound is allyl methacrylate.

19. The process of claim 1, wherein the unsaturated compound is allyl glycidyl ether.

20. The process of claim 1 where the unsaturated compound is an allyl or methallyl polyether.

21. The process of claim 1 where the reaction is carried out at a temperature of −50 ° C. to 250 ° C.

22. The process of claim 1 where the reaction is conducted in the presence of a solvent chosen from a hydrocarbon, a halogenated hydrocarbon, an ether, an alcohol, or a combination of two or more thereof.

23. The process of claim 1, wherein the platinum concentration is from about 100 parts per billion to about 100 parts per million.

* * * * *